United States Patent [19]

Utsugi

[11] 4,066,070
[45] Jan. 3, 1978

[54] TUBULAR MEDICAL INSTRUMENT HAVING A FLEXIBLE SHEATH WITH CUFFS

[75] Inventor: Mikio Utsugi, Machida, Japan

[73] Assignee: Olympus Optical Co., Ltd., Tokyo, Japan

[21] Appl. No.: 701,075

[22] Filed: June 30, 1976

[30] Foreign Application Priority Data

June 30, 1975 Japan ............................ 50-91455[U]

[51] Int. Cl.² ............................................... A61B 1/00
[52] U.S. Cl. ...................................... 128/4; 128/2 M; 128/349 B; 128/DIG. 9
[58] Field of Search ........................................ 128/4–8, 128/2 M, DIG. 9, 349 R, 349 B, 348, 350 R

[56] References Cited

U.S. PATENT DOCUMENTS

| | | | |
|---|---|---|---|
| 2,855,934 | 10/1958 | Daughaday, Jr. | 128/349 R |
| 3,485,237 | 12/1969 | Bedford | 128/2 M |
| 3,665,928 | 5/1972 | Del Guercio | 128/350 R |
| 3,895,637 | 7/1975 | Choy | 128/348 |

FOREIGN PATENT DOCUMENTS

| | | | |
|---|---|---|---|
| 1,278,965 | 11/1961 | France | 128/349 R |
| 1,170,586 | 5/1964 | Germany | 128/DIG. 9 |

*Primary Examiner*—Robert W. Michell
*Assistant Examiner*—Henry S. Layton

[57] ABSTRACT

Main and auxiliary cuffs made of an elastic material such as rubber, etc., are mounted in close proximity to each other on the forward end portion of a flexible sheath of a tubular medical instrument. The flexible sheath is inserted into a body cavity of a human being and with further insertion of the flexible tube the main cuff is contacted, while at the expanded state, with the wall surface of the body cavity and when the flexible sheath is forwardly pushed the portion of the main cuff is rearwardly deformed, while effecting a rolling contact with the wall surface of the body cavity, to permit it to ride on the auxiliary cuff. When the auxiliary cuff is then expanded to cause the corresponding wall surface of the body cavity to be expanded, the main cuff is separated away from the wall surface of the body cavity to cause the portion of the main cuff to be forwardly pushed ahead into an original position. Such a step is cyclically repeated so that the sheath can be intermittently advanced into the body cavity of the human being.

5 Claims, 19 Drawing Figures

TUBULAR MEDICAL INSTRUMENT HAVING A FLEXIBLE SHEATH WITH CUFFS

BACKGROUND OF THE INVENTION

This invention relates to a tubular medical instrument including as an instrument body a cuff-equipped flexible sheath, such as a sound, a catheter, a flexible tube of an endoscope and so on, which is adapted to be inserted into a body cavity (for example, a small intestine) of a human being for medical treatment.

According to a conventional method a flexible tube of such a medical instrument is inserted into a body cavity, such as a stomach, a small intestine etc., of a human being, for example, according to the peristalysis of a small intestine. This method, however, requires a longer time for insertion of the flexible tube, giving pain to the patient. Another method is to insert a flexible tube of such a medical instrument into a body cavity of human being by positively applying a push to the flexible tube. With further insertion of the flexible tube an increased resistance is encountered between the wall surface of the body cavity and the outer surface of the tube and a pushing force is not fully transmitted to the tip portion of the flexible tube. An increased pushing force imparts an increased resistance to the wall surface of the body cavity of the patient, giving a great deal of pain to the patient.

Particularly, an intestinoscope for observing a small intestine is inserted into the small intestine through a long passage consisting of the oral cavity, esophagus, stomach and duodenum. Since many bend portions are present in the long passage, a conventional intestinoscope, when inserted thereinto, imparts a relatively strong pressure to the wall of the bend portions of the passage of the human body, making it difficult to permit further insertion due to its frictional resistance and thus causing great pains to the patient. For this reason, the distance at which the intestinoscope can be inserted into the small intestine is restricted to merely 30 to 80 cm as measured from the entrance of the small intestine. For this reason, there is a demand for a medical instrument equipped with a flexible sheath adapted to be smoothly inserted up to a desired portion of a body cavity of a patient without giving any excess pain to the patient.

SUMMARY OF THE INVENTION

It is accordingly the object of this invention to provide a tubular medical instrument equipped with a flexible sheath capable of being smoothly and rapidly inserted up to a desired portion of a body caivty of a patient without involving any increased increases friction between the wall surface of the body cavity and the outer surface of the sheath and in consequence without imparting any excess pain to the patient.

To attain such an object, main and auxiliary cuffs are mounted either in a set or several sets particularly on the forward portion of a sheath of a medical instrument with the main cuff immediately behind the auxiliary cuff. By selectively supplying air to the main and auxiliary cuff and selectively drawing it from them the sheath can be prevented from being intimately contacted with the wall surface of the body cavity of a human being and can be smoothly inserted further into the body cavity without involving any excess friction between the wall surface of the body cavity and the outer surface of the sheath.

When the sheath according to this invention is inserted into the body cavity of the patient there is involved a resistance resulting from an elastic deformation of the main cuff and a very small rolling friction produced when the main cuff is dimensionally deformed while effecting a rolling contact with the wall surface of the body cavity. According to this invention, therefore, insertion can be readily effected into the body cavity of the patient without giving any excess pain to the patient.

Cuff or balloon-equipped medical instruments are conventionally known in the art. However, most of the conventional cuffs or balloons are used to hold the sheath in proper position in the body cavity of a patient and do not perform the function of readily and smoothly inserting the sheath further into the body cavity of the patient as in the case of this invention. This invention, therefore, constitutes a significant departure from the prior art.

DETAILED DESCRIPTION OF THE PREFERRED EMBODIMENTS

Figure 1:
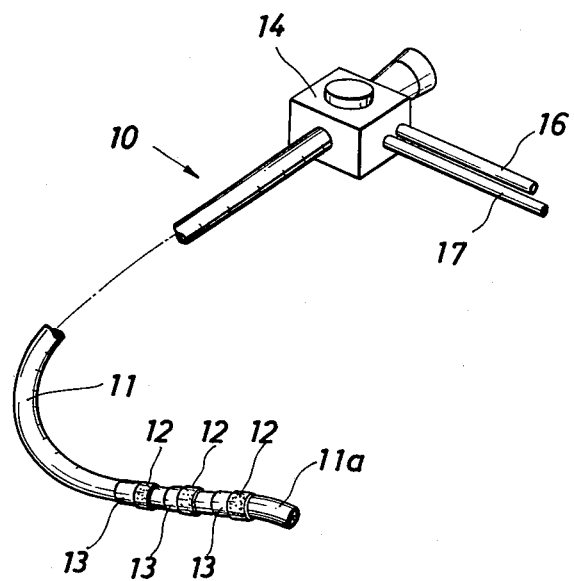
FIG. 1 is a perspective view, partly omitted, showing a tubular medical instrument equipped with cuffs according to one embodiment of this invention.
Figure 2:
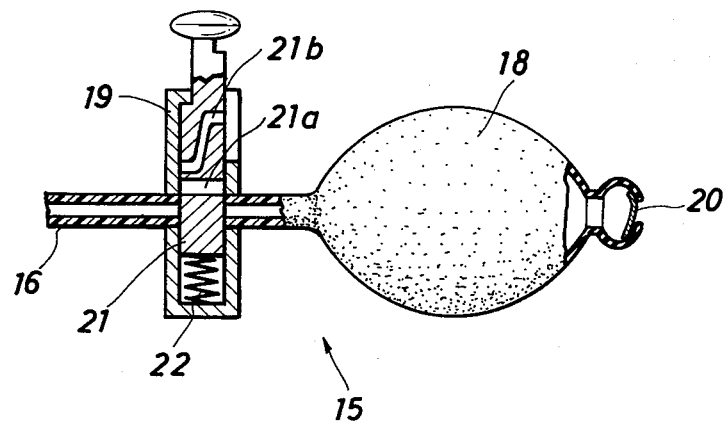
FIG. 2 is an enlarged view, partly in section and partly broken away, showing a gas control device adapted to supply a gas to the cuffs and draw it from them.

FIG. 1 shows a flexible sheath equipped endoscope 10 according to this invention which is used as a medical instrument. Three sets of main and auxiliary cuffs 12 and 13 are fitted at predetermined distances on the forward end portion 11a of a flexible sheath 11 in the endoscope 10. The set of main and auxiliary cuffs 12 and 13 are shown to an enlarged scale in FIG. 3 and the operation will be explained below. An air supply device 15 in FIG. 2 is adapted to supply the air from a control section 14 through a flexible sheath 11 to the main and auxiliary cuffs 12 and 13 and draw it from the main and auxiliary cuffs 12 and 13 through the flexible sheath 11 to the control section 14. The air supply device 15 is connected through a connection pipe 16 to the control unit 14 in FIG. 1 and the connection pipe 16 is used for the operation of the main cuff 12. Like the connection pipe 16 a connection pipe 17 has one end connected to the control section 14 and the other end (not shown)

connected to a device similar to the air supply device in FIG. 2. The connection pipe 17 is used for the operation of the auxiliary cuff 13. In FIG. 2 the air supply device 15 includes a pressure bulb 18 adapted to be squeezed by an operator's fingers and a direction control valve 19 disposed between the bulb 18 and the pipe 16. The bulb 18 is equipped with a check valve 20. The valve 19 includes a valve member 21 adapted to be slidably movable, when depressed by an operator's finger, against an urging force of a spring 22 and has a passage 21a for permitting the pipe 16 to communicate with the bulb 18 and a passage 21b for permitting the pipe 16 to be exposed to an outer atmosphere. When the pipe 16 is caused to communicate with the passage 21a of the valve member 21 the gas can be sent to the pipe 16 by the operation of the bulb 18 and when the pipe 16 is caused to communicate with the other passage 21b of the valve member 21 the pressure gas in the pipe 16 can be sent out toward the outer atmosphere.

Figure 3:
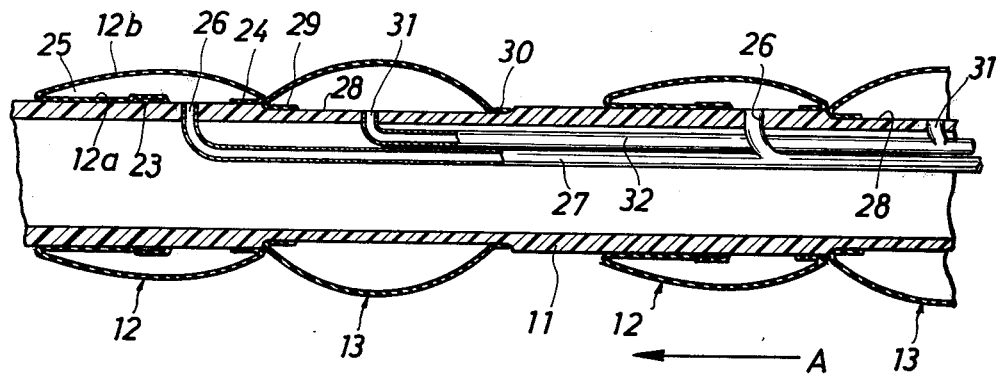
FIG. 3 is an enlarged, longitudinal cross-sectional view showing the forward portion of a sheath of the medical instrument in FIG. 1.

An arrow A in FIG. 3 shows a direction in which a flexible sheath 11 is advanced. The direction may be taken as a direction in which the sheath 11 is introduced into the body cavity of a human being. In FIG. 3 the forward portion 11a of the flexible sheath 11 is shown and the tip portion of the flexible sheath 11 and various fiber bundles disposed in the sheath 11 are omitted for brevity sake.

A forward end portion 23 and rear end portion 24 of the main cuff 12 are liquid-tightly fixed by a suitable bonding means to the outer periphery of the flexible sheath 11. Easily deformable, pliable material such as natural rubber, synthetic rubber such as Neoprene (du Pont de Nemours & Co., Ltd.), rubber latex, etc., is suitable for the material of the main cuff. The main cuff is formed by inserting a double open-ended cylindrical member, which is substantially equal to and somewhat smaller than the other diameter of the sheath 11, over the outer periphery surface of the sheath 11, inwardly bending both the end portions of the cylindrical member with one end portion bent deeply to provide a doubled back section 25, and bonding each end portion of the cylindrical member to the outer periphery of the sheath. The doubled back section 25 is normally placed, as shown in FIG. 3, ahead of the forward bonded end portion 23 of the main cuff 12. In consequence, the main cuff 12 as measured in the longitudinal direction of the sheath 11 is far longer than a distance between the bonded end portion of the main cuff 12, for example, about two times as long as the distance between the bonded end portions 23 and 24 of the main cuff 12. An air hole 26 is opened in that area of the sheath 11 which is located between the bonded end portions of the cylindrical member. Each air hole 26 in the sheath 11 communicates with a common air supply pipe 27 the base end of which communicates with the pipe 16 through the control section 14. Immediately behind the main cuff 12 is formed a circumferential depression 28 which extends a predetermined distance in the longitudinal direction of the sheath 11. The auxiliary cuff 13 is located in the depression 28 in the sheath 11. The auxiliary cuff 13 is made of a material substantially similar to that of the main cuff 12 and is formed by inserting a cylindrical member, substantially equal to the outer diameter of the depressed section 28 of the sheath 11, over the sheath 11 and liquid-tightly fixing front and rear end portions 29 and 30 of the cylindrical member to the outer peripheral surface of the sheath 11 by means of a suitable bonding means. The front end portion 29 of the auxiliary cuff 13 is located adjacent to the rear end portion 24 of the main cuff 12. The auxiliary cuff 13 has no doubled back section corresponding to that of the main cuff 12. An air hole 31 is formed in that area of the sheath 11 which is located between the front and rear end portions 29 and 30 of the auxiliary cuff 13 and each air hole 31 in the sheath 11 communicates with a common air supply pipe 32 the base end of which communicates with the pipe 17 through the control section 14.

As mentioned above, the three sets of main and auxiliary cuffs 12 and 13 are placed at predetermined intervals on the forward portion 11a of the sheath 11. A single set of main and auxiliary cuffs 12 and 13 may be provided on the forward end portion 11a of the sheath 11 or a plurality of sets of main and auxiliary cuffs 12 and 13 may be provided substantially over the whole length of the sheath 11 as required.

The process of inserting the flexible sheath 11, for example, into a small intestine of a human body will be explained below by referring to FIGS. 4(a) to 4(f).

Figure 4A:
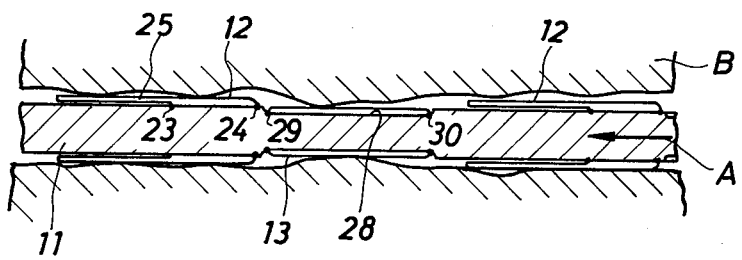
FIGS. 4(a) to 4(f), each, are an explanatory view showing the various states of the cuffs in FIG. 3.
Figure 4B:
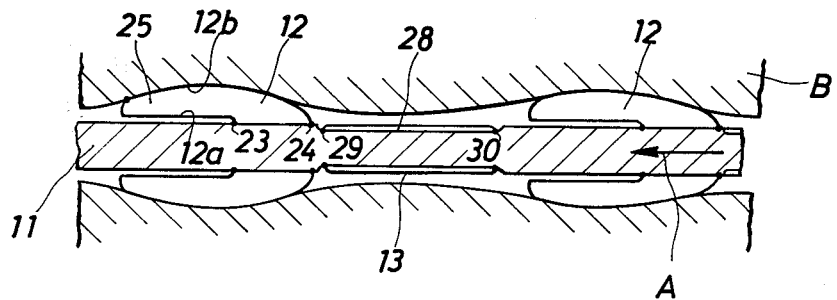
Figure 4C:
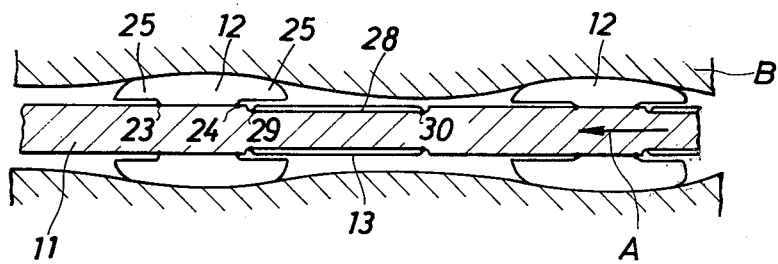
Figure 4D:
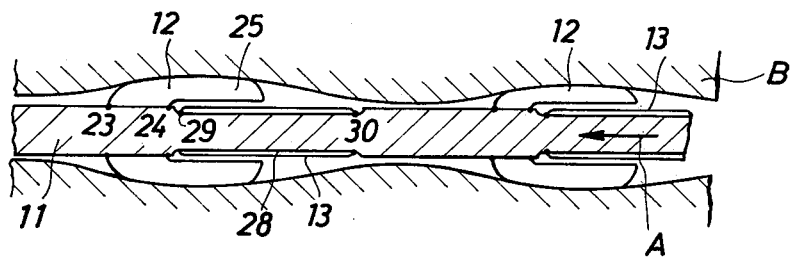
Figure 4E:
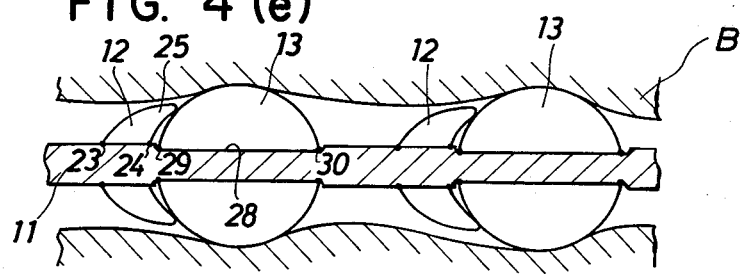

In FIGS. 4(a) to 4(f) only the forward portion 11a of the sheath 11 is shown for convenience of explanation. The sheath 11 is introduced into the body cavity (B) of the human being with the main and auxiliary cuffs 12 and 13 intimately contacted with, or flattened with respect to, the outer periphery surface of the sheath 11. Upon further inserting the sheath 11 into the body cavity (B) of the human being an increased resistance is encountered between the outer peripheral surface of the sheath 11 and the wall surface of the body cavity (B). As a result, difficulty is experienced with an increasing extent. With this in mind the operator sends air into the main cuffs 12 only as shown in FIG. 4(b) to cause them to be expanded. That is, an upper portion 12b of the so far flattened doubled back portion of the main cuff 12 is expanded in the radial direction of the sheath 11 into engagement with the wall surface of the body cavity (B) to cause the body cavity to be pushed in the radial direction of the body cavity. In this state, the forward section 11a of the sheath 11 per se is separated away from the wall surface of the body cavity so that the sheath 11 can be further advanced, in a direction as indicated by an arrow A, upon being further pushed in the forward direction. When the sheath 11 is so advanced into the body cavity (B) of the human being, the radially expanded main cuff 12 is so deformed that the doubled back section 25 is gradually increased in the rearward direction of the sheath 11 as shown in FIGS. 4(c) and 4(d). During this time period that area of the main cuff 12 which is in contact with the wall surface of the body cavity (B) is continuously changed in its outer portion 12b without involving a substantially relative slippage. In consequence, a rolling contact is effected between the doubled back section 25 of the main cuff 12 and the wall surface of the body cavity (B), and a resistance encountered during the deforming movement of the main cuff 12 from the state as shown in FIG. 4(b) to the state as shown in FIG. 4(c) includes a deformation resistance resulting from the flexible material of the main cuff 12 and a friction resulting from the rolling contact. As a whole, only a slight resistance is involved in a direction opposite to the direction as indicated by the arrow A, since the material of the main cuff 12 is very pliable in nature and since a very slight resistance is experienced during the rolling contact of the main cuff 12 with the wall surface of the body cavity (B). In this way, the sheath 11 can be very smoothly advanced, in the direction of the arrow A, by an amount corresponding to the deforming movement of the main cuff 12.

Figure 4F:
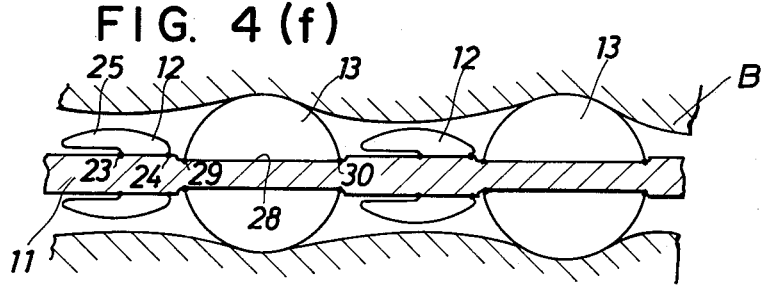

With each main cuff 12 at the expanded state air is supplied into each auxiliary cuff 13 to cause the latter to be fully expanded to permit the body cavity (B) to be pushed in the radial direction of the body cavity. By so doing that upper portion 12b of the main cuff 12 which has been in contact with the body cavity (B) is separated away from the outer wall of the body cavity (B). That is, that doubled back section 25 of the main cuff 12 which has covered substantially one half of the auxiliary cuff as shown in FIG. 4(d) is gradually pushed ahead with an increasing expansion of the auxiliary cuff 13, i.e., with an increasing inclination angle of the auxiliary cuff 13. The main cuff 12 is gradually moved ahead, while deformed, until at least that doubled back section 25 of the main cuff 12 assumes the state as shown in FIG. 4(f), i.e., the state as shown in FIG. 4(b). The deforming forward movement of the main cuff 12 is effected by two functions of the auxiliary cuff 13, i.e., one function of separating the main cuff 12 away from the auxiliary cuff 13 and the other function of pushing the main cuff 12 ahead to the original position.

Then, the air is drawn from the auxiliary cuff 13 to permit each auxiliary cuff 13 to be brought back into the original state as shown in FIG. 4(b). If such an operation is cyclically repeated, the sheath 11 can be further advanced intermittently into the body cavity (B) of the human being.

Since the auxiliary cuff 13 is mounted on the depression 28 in the sheath 11, when the main cuff 12 is moved, while deformed in the rearward direction of the sheath 11, the main cuff 12 can smoothly ride on the auxiliary cuff 13 without being subjected to any resistance.

In order to attain a smooth introduction of the sheath 11 into the body cavity of the human being (B), the following requirements will be required.

Figure 5:
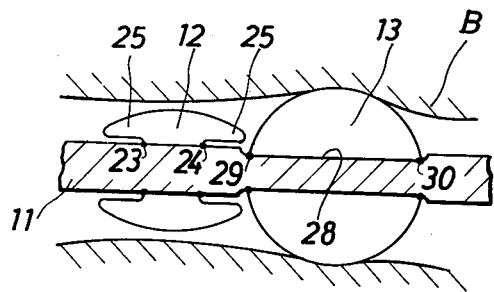
FIGS. 5(a) and 5(b) are undesirable examples shown merely by way of comparison.
Figure 5:
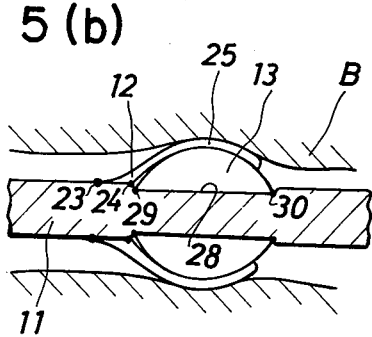

1. The main cuff 12 is located in close proximity to the auxiliary cuff 13.
2. The main cuff 12 has no excess doubled back section 25. FIG. 5(a) shows the case where the requirement (1) is not satisfied. In the FIgure like reference numerals are employed to designate parts or elements corresponding to those shown in the first embodiment. Suppose that a rear end portion 24 of the main cuff 12 is spaced a considerable distance away from a front end 29 of an auxiliary cuff 13. When in this case the auxiliary cuff 13 is expanded (cf., FIG. 4(e)), the main cuff 12 is not fully pushed ahead and a doubled back section 25 is projected at each side of the main cuff 12. Since no sufficient deforming movement of the main cuff 12 is effected, a sheath 11 is advanced a little amount in one cycle.

FIG. 5(b) shows the case where the requirement (2) is not satisfied. In this Figure, like reference numerals are employed to designate parts or elements corresponding to those shown in the first embodiment. In this case, a doubled back section 25 of a main cuff 12 covers more than one half of an auxiliary cuff 13 and, even if the auxiliary cuff 13 is expanded, the main cuff 12 is sandwiched between the wall surface of the body cavity (B) and the auxiliary cuff 13, preventing the main cuff 12 from being pushed ahead into the original position. In order to push the main cuff 12 ahead of the original position (see FIG. 4(e)) by expanding the auxiliary cuff 13 it is necessary for the doubled back section of the auxiliary cuff 13 not to extend beyond the midpoint of the expanded auxiliary cuff 13. But in a third embodiment of this invention as will be later described the second requirement will not be necessarily required.

Figure 6:
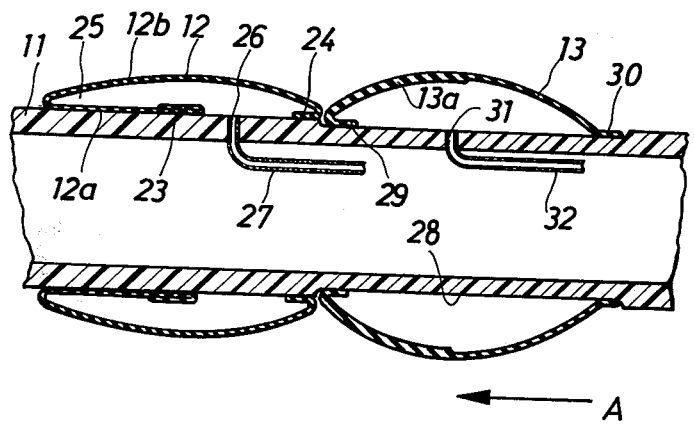
FIG. 6 is a longitudinal cross-sectional view showing a tubular medical instrument equipped with cuffs according to a second embodiment of this invention.
Figure 7:
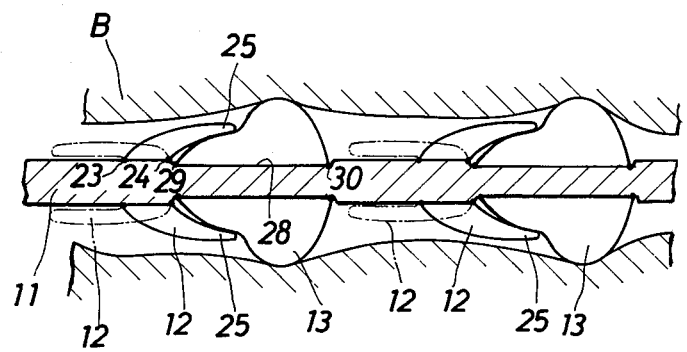
FIG. 7 is a schematic explanatory view for explaining the operative state of the cuffs mounted on a sheath in FIG. 6.
Figure 8:
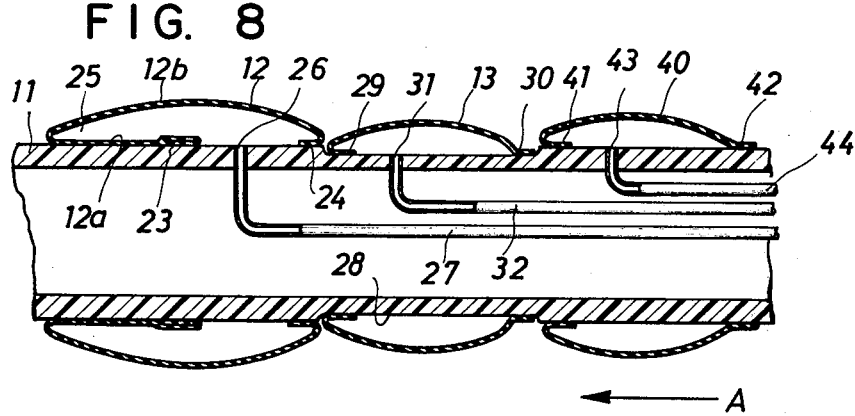
FIG. 8 is a longitudinal cross-sectional view showing a tubular medical instrument equipped with cuffs according to a third embodiment of this invention.
Figure 9A:
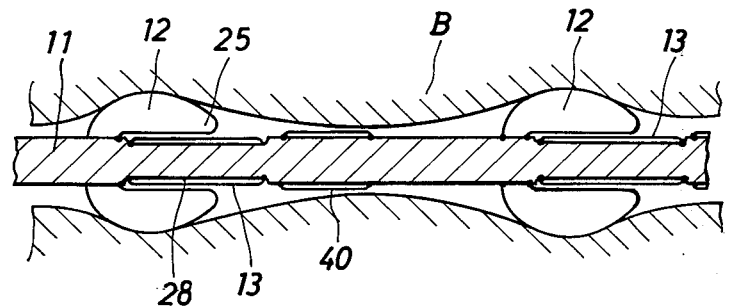
FIGS. 9(a) to 9(e) are explanatory views showing the various operative states of the cuffs mounted on a sheath in FIG. 8.
Figure 9:
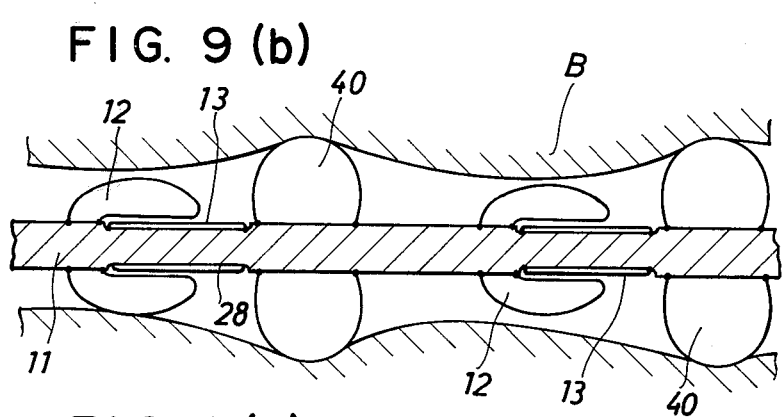
Figure 9:
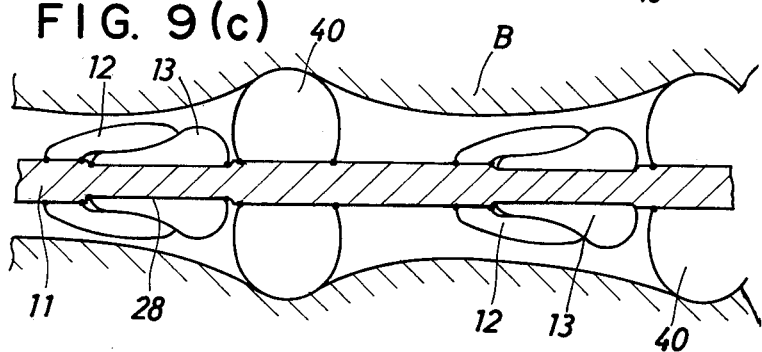
Figure 9:
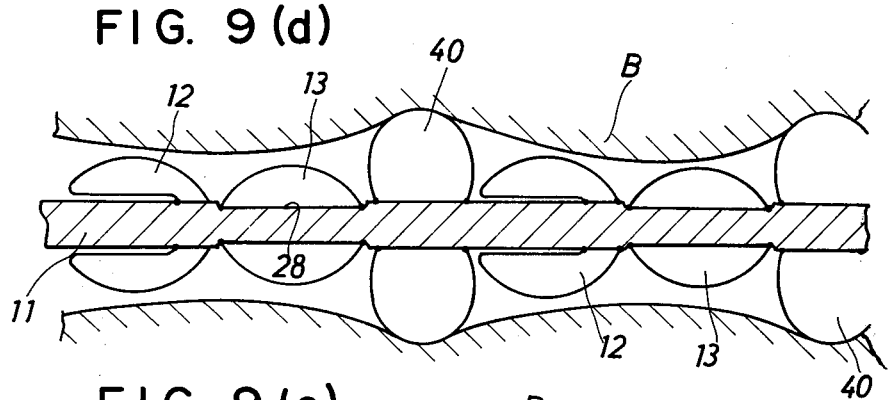
Figure 9:
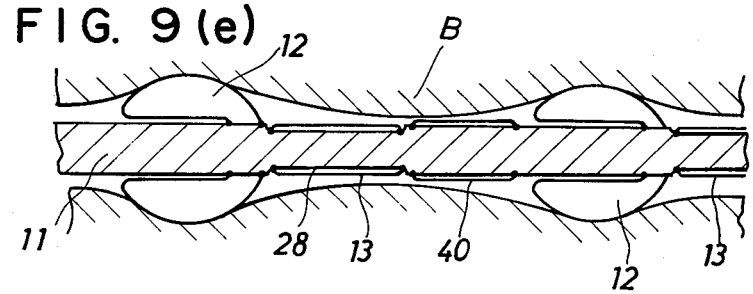

FIGS. 6 and 7 show a second embodiment of this invention. In these Figures like reference numerals are employed to designate parts or elements corresponding to those shown in the first embodiment. In this embodiment different portions or sections of the parts or elements will be emphatically explained below.

As shown in FIG. 6 an auxiliary cuff 13 is thickened substantially over the forward half section 13a of the auxiliary cuff 13. For example, the forward half portion 13a of the auxiliary cuff 13 has a thickness 2 to 3 times that of the rest of the auxiliary cuff 13. In consequence, the auxiliary cuff 13 is more easily expandable at the backward half portion than at the forward half portion 13a. When the auxiliary cuff 13 is expanded (cf., FIG. 4(e)), that portion 13a of the auxiliary cuff 13 which is in contact with a doubled back section 25 of a main cuff 12 is expanded to a lesser extent as shown in FIG. 7. On the other hand, the backward half section is fully expanded. As a result, the main cuff 12 can be more positively separated away from the wall surface of the body cavity (B). Although the forward half portion 13a of the auxiliary cuff 13 is not more sharply expanded than the backward half portion, it has an inclined surface sharp enough to push the doubled back section 25 of the main cuff 12 ahead to the original position as indicated by a dot dash line in FIG. 7.

FIGS. 8 and 9(a) to (e) show a third embodiment of this invention. In these Figures like reference numerals are employed to designate parts or elements corresponding to those shown in the first embodiment and different portions or sections of the parts or elements will be emphatically explained below.

In this embodiment main and auxiliary cuffs 12 and 13 are substantially similar in arrangement to those shown in the first embodiment. Another auxiliary cuff 40 is located behind the auxiliary cuff 13. The auxiliary cuff 40 is formed by inserting a double open-ended cylindrical member, made of a material the same as that of the main and auxiliary cuffs 12 and 13, over a sheath 11 and bonding front and rear end portions 41 and 42 in a liquid-tight fashion to the outer peripheral surface of the sheath 11. An air hole 43 is formed in that portion of the sheath 11 which is located between the front and rear end portions 41 and 42. The air hole 43 in the sheath 11 communicates with an air supply pipe 44. Although the base end of a pipe 44 is not shown in FIGS. 8 and 9(a) to (e), it extends up to a control section, like the other pipes 27 and 32, where it communicates with an air feed pipe. The main cuff 12 and auxiliary cuffs 13 and 40 all constitute a set. Several sets, for example, three sets are mounted on the sheath 11.

The operation of the third embodiment will be explained below.

The sheath 11 is introduced into the body cavity (B) of the human being with each cuff unexpanded or flattened. With further insertion of the sheath 11, difficulty is encountered due to an increased friction between the wall surface of the body cavity (B) and the sheath 11. At this time the main cuff is expanded into contact with the wall surface of the body cavity (B) and then the sheath 11 is pushed ahead, causing the main cuff 12 to be rearwardly deformed in its demension to permit a doubled back section 25 of the main cuff 12 to ride on the auxiliary cuff 13. Thereafter, air is fully supplied to the auxiliary cuff 40 to cause the latter to be expanded as shown in FIG. 9(b) to permit the wall surface of the body cavity (B) to be enlarged in the radial direction of the body cavity, and then air is also supplied to the auxiliary cuff 13 to cause the latter to be expanded enough for the double back section 25 of the main cuff 12 to be returned to its original position. By so doing the doubled back section 25 of the main cuff 12 is smoothly pushed, while deformed, ahead to the original position. That is, the auxiliary cuff 13 performs the function of pushing the doubled back section 25 of the main cuff 12 ahead to the original position and the auxiliary cuff 40 performs the function of separating the main cuff 12 away from the wall surface of the body cavity (B).

Since the different auxiliary cuffs 13 and 40 are mounted on the sheath 11, the body cavity of the human being can be radially enlarged to permit the main cuff 12 to be separated away from the wall surface of the body cavity.

After each main cuff is returned to the original position as shown in FIG. 9(d) the air is drawn from the auxiliary cuffs 13 and 40 as shown in FIG. 9(e), causing the auxiliary cuffs 13 and 40 to be brought back to the original position. If the above-mentioned operation is cyclically repeated, the sheath 11 is advanced intermittently and smoothly into the body cavity of the human body.

What is claimed is:

1. A tubular medical instrument comprising:
    an elongated flexible sheath for insertion into a body cavity of a human body;
    a radially expansible main cuff having a doubled back section on an outer peripheral surface of one end of the flexible sheath and also having outer surfaces which, when said sheath is inserted in the body cavity, are normally in contact with a wall surface of the body cavity when the main cuff is expanded;
    means for supplying air to said main cuff to expand same, said outer surfaces, when said main cuff is expanded in said body cavity, being continuously deformed in a first direction upon movement of said sheath in said body cavity in a second opposite direction corresponding to that in which the flexible sheath is inserted into the body cavity, without involving substantial slippage;
    a radially expansible auxiliary cuff mounted on a portion of the outer peripheral surface of the flexible sheath which is close to the main cuff and is opposite to said one end of the flexible sheath with respect to the main cuff;
    said doubled back section riding on the auxiliary cuff as the main cuff is being deformed in the first direction during the insertion of the flexible sheath; and
    means for supplying air to said auxiliary cuff to expand same to separate the outer surfaces of the main cuff from the wall surface of the body cavity and to push the doubled back section away from the auxiliary cuff into an original position of the doubled back section with respect to the main cuff.

2. A tubular medical instrument according to claim 1, in which said doubled back section of the main cuff rides on said auxiliary cuff substantially up to a midpoint thereof.

3. A tubular medical instrument according to claim 1, in which said auxiliary cuff has a portion located close to said main cuff and formed thicker than the rest of said auxiliary cuff.

4. A tubular medical instrument according to claim 1, in which one portion of said outer peripheral surface of said flexible sheath is formed smaller is diameter than the rest of flexible sheath, and said auxiliary cuff is mounted on said one portion.

5. A tubular medical instrument according to claim 1, in which another radially expansible auxiliary cuff is mounted on an outer peripheral surface portion of said flexible sheath which is remote from said main cuff with respect to the first said auxiliary cuff, said other cuff having means for supplying air thereto to radially expand same and cause the corresponding wall surface of the body cavity to be radially expanded to permit the outer surfaces of said main cuff to be separated from the wall surface of the body cavity which was in contact with the outer surfaces of said main cuff.

* * * * *